April 17, 1945. H. E. CORNELL Plant Pat. 657
ORANGE TREE
Filed Aug. 15, 1944
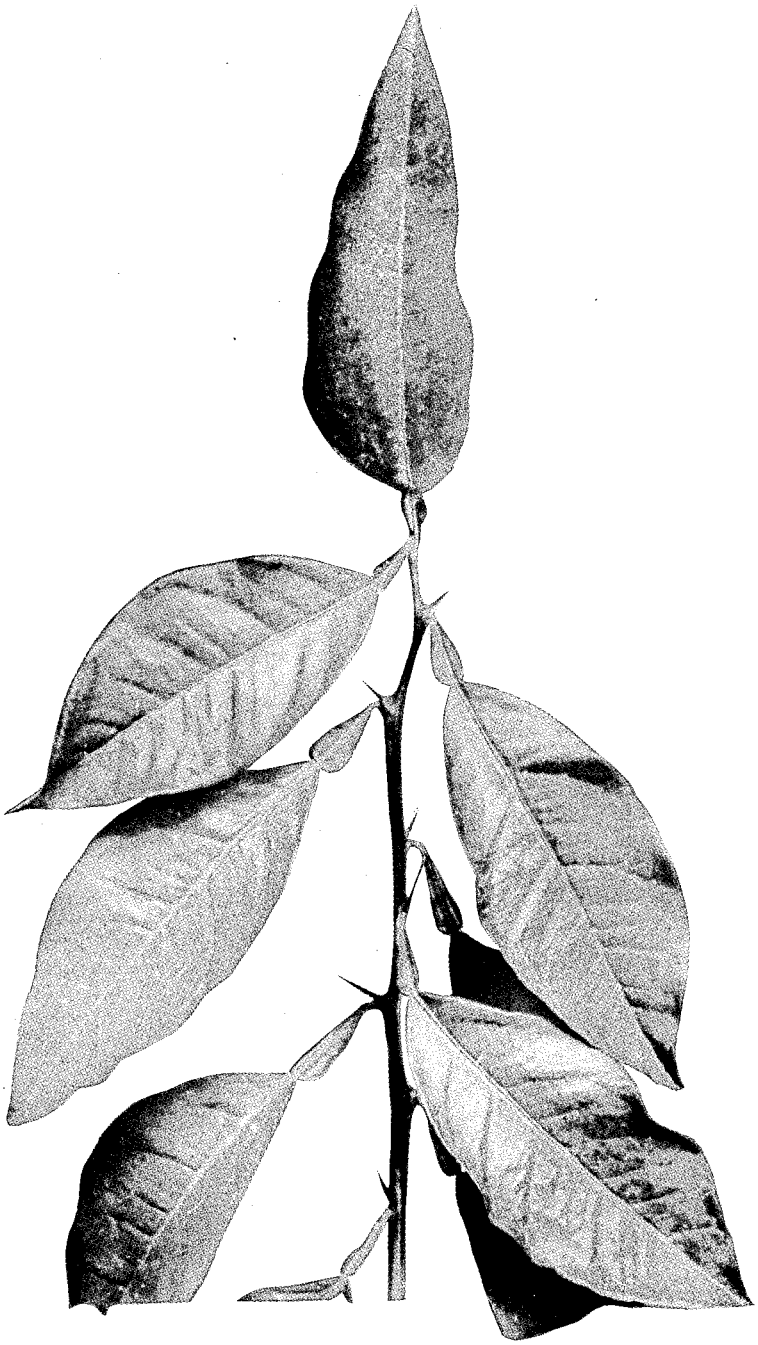
INVENTOR
HAROLD E. CORNELL, DECEASED
BY THELMA CORNELL, ADMINISTRATRIX
BY Roy F. Steward
ATTORNEY Patented Apr. 17, 1945

Plant Pat. 657

UNITED STATES PATENT OFFICE

657

ORANGE TREE

Harold E. Cornell, deceased, late of Winter Haven, Fla., by Thelma Cornell, administratrix, Winter Haven, Fla., assignor to Thelma H. Cornell, Winter Haven, Fla.

Application August 15, 1944, Serial No. 549,569

1 Claim. (Cl. 47—62)

This discovery relates to a new variety of orange tree and the fruit thereof, well adapted for cultivation in Florida and earlier to mature than any variety heretofore grown there.

The new orange originated as a sport in the top of a Parson Brown orange tree on a sour orange root planted out in 1912. This tree was in a grove located near Dundee, Florida, belonging to my late husband, Harold E. Cornell, and the new variety was discovered by him in 1938 when fruit on said tree was being checked for maturity. Thereafter, fruit from the sport branch was tested every year for four years, and it consistently passed the test 5 to 8 weeks earlier than did fruit on other parts of the same tree and on adjacent trees of the Parson Brown variety. The sport branch occupies somewhat less than one quarter of the entire tree top and has produced several boxes of the new variety fruit each year since it was discovered.

Reproduction of the new variety, both by topworking other trees with buds from the sport branch and also by budding different kinds of root stock, was commenced by my late husband and has since been continued by me. I now have more than 240 trees on rough lemon stock topworked to the new variety which are bearing some fruit this season. These are in grove planting and were developed by cutting off the tops of bearing grapefruit trees in grove and budding them over. I have also set out this summer, 100 2-year-old trees of the new variety, which already have nice branches. Also, I have 15 acres planted with 1½-year-old seedlings in grove form which I intend to bud with the new variety next spring.

No budded stock from the branch sport has been sold or exhibited.

The new variety of orange tree is distinctively characterized by the fact that the new growth, especially, has a tendency to be thorny, as shown in the accompanying photographic illustration.

The color and shape of the fruit itself, however, are not definitely distinctive, and hence the fruit is not here illustrated. The fruit is oblong-rounded in form, medium to large in size, and deep yellow to orange in color at maturity. Other general characteristics of the new orange are: size, medium to large; sections or segments, 9 or 10; seeds, zero to 5; juice abundant, orange colored; sweetness and acidity well blended; flavor, delicious and pleasing.

The following important distinguishing characteristics and advantages of the fruit produced by the new variety of orange tree have now been well established:

1. The fruit passes the maturity test prescribed by Florida law considerably earlier, usually as much as 5 to 8 weeks earlier, than any other orange variety now grown in and marketed from Florida.

2. Because of its early blending of acidity and sweetness, it is always at least equal to and generally surpasses in quality any other early orange now grown in Florida.

3. It retains its high quality for a long period of time while still remaining on the tree.

The figures given in the subjoined table are typical of the results of maturity tests, made under the conditions prescribed by the Florida law, upon the new variety of orange in comparison with two other well known early oranges now commercially grown in Florida, on the dates indicated:

| | October 2 | | November 7 | |
|---|---|---|---|---|
| | New Orange | Hamlin | New Orange | Parson Brown |
| Brix reading | 10.00 (29° C.) | 10.60 (28° C.) | 11.10 (21° C.) | 10.10 (22° C.) |
| Temperature correction | 0.75 | 0.70 | 0.20 | 0.30 |
| Total soluble solids per cent | 10.75 | 11.30 | 11.30 | 10.40 |
| Burette reading | 10.9 | 20.5 | 8.1 | 14.6 |
| Acid per cent | .84 | 1.58 | .62 | 1.12 |
| Ratio total solids to acid | 12.79 to 1 | 7.15 to 1 | 18.20 to 1 | 9.28 to 1 |

Such results definitely and graphically establish the early maturity and high quality characteristics of the new orange variety herein disclosed.

What is claimed is:

A new and distinct variety of orange tree, substantially as described, characterized by the tendency of its new growth to be thorny; and by fruit which matures considerably earlier, commonly 5 to 8 weeks earlier, than any other variety of orange now grown in Florida and which nevertheless, because of the blending of its acidity and sweetness, has high quality characteristics at such early maturity.

THELMA CORNELL.

*Administratrix of the Estate of Harold E. Cornell, Deceased.*